(12) United States Patent
Wada

(10) Patent No.: US 6,719,743 B1
(45) Date of Patent: Apr. 13, 2004

(54) SANITARY TAMPON

(75) Inventor: Mitsuhiro Wada, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 356 days.

(21) Appl. No.: 09/606,328

(22) Filed: Jun. 29, 2000

(30) Foreign Application Priority Data

Jul. 2, 1999 (JP) ............................................. 11-189196

(51) Int. Cl.[7] ................................................. A61F 13/20
(52) U.S. Cl. .................................. 604/385.18; 604/904
(58) Field of Search ............................. 604/11–18, 904, 604/385.18

(56) References Cited

U.S. PATENT DOCUMENTS

| 3,306,295 A | | 2/1967 | Penksa ........................ 128/285 |
| 3,340,874 A | | 9/1967 | Burgeni ....................... 128/285 |
| 4,266,546 A | * | 5/1981 | Roland et al. ............... 604/365 |
| 4,573,988 A | | 3/1986 | Pieniak ........................ 604/379 |
| 4,755,166 A | * | 7/1988 | Olmstead ..................... 604/11 |
| 5,350,371 A | | 9/1994 | Van Iten ...................... 604/398 |
| 5,445,605 A | * | 8/1995 | Pluss ............................ 604/11 |
| 5,533,990 A | * | 7/1996 | Yeo .............................. 604/12 |
| 5,592,725 A | | 1/1997 | Brinker ........................ 28/118 |
| 5,797,894 A | | 8/1998 | Cadieux ....................... 604/378 |
| 5,807,372 A | * | 9/1998 | Balzar .................... 604/385.18 |
| 6,283,952 B1 | * | 9/2001 | Child et al. .................... 28/118 |

FOREIGN PATENT DOCUMENTS

| EP | 0422660 A1 | 4/1991 | | |
| EP | 05068695 | 3/1993 | | |
| GB | 866023 | 4/1961 | | |
| JP | 1-146548 | 6/1989 | | |
| JP | 3-146058 | 6/1991 | | |
| JP | 05068695 | 3/1993 | | |
| WO | WO-99/32061 | 7/1999 | | |
| WO | WO 00/23024 | * | 4/2000 | ........... A61F/13/15 |

* cited by examiner

*Primary Examiner*—Weilun Lo
*Assistant Examiner*—C. Lynne Anderson
(74) *Attorney, Agent, or Firm*—Darby & Darby

(57) ABSTRACT

There is disclosed a sanitary tampon including an absorber including: an absorbent layer made of an absorbent fibrous material; and a hydrophobic liquid-permeable layer covering the absorbent layer. The absorber is formed firstly into a flat shape and then into a column shape. The absorbent layer forming the flat absorber is formed with a plurality of small recesses which open in the surface of the absorbent layer and extend into the absorbent layer.

7 Claims, 7 Drawing Sheets

SANITARY TAMPON

BACKGROUND OF THE INVENTION

1. Field of the Invention

The present invention relates to a sanitary (hygienic) tampon to be inserted into a vagina for absorbing the menstrual blood.

2. Description of the Related Art

In recent years, a variety of products have been developed as the sanitary tampon. In Japanese Patent Laid-Open No. 146548/1989, for example, there is disclosed a sanitary tampon which is constructed to include an absorber made of hydrophilic fibers and an outer layer made of a hydrophobic sheet having hydrophilic fibers mixed therein. In Japanese Patent Laid-Open No. 146058/1991, on the other hand, there is disclosed a tampon which is constructed to include a column-shaped highly compressed core and an outer wall. In Japanese Patent Laid-Open No. 68695/1993, moreover, there is disclosed a tampon in which a sheet of a high fiber density and a sheet of a low fiber density are combined so that the sheet of a low fiber density may partially appear in the surface when the tampon is formed into a column shape. In these tampons, the absorbent fiber material is compressed and formed into the column shape, and this compression is released by absorbing the menstrual blood when the tampon is used. As a result, the tampon swells to close the vaginal opening and absorbs the menstrual blood which is then continuously discharged.

However, the menstrual blood is so highly viscous that it hardly migrates into the central portion of the tampon of the related art but resides on the surface of the tampon. This lowers the absorption rate of the menstrual blood so that the compressed tampon takes a long time to restore its bulk. When much menstrual blood is discharged, on the other hand, it cannot be fully absorbed by the tampon, or the vaginal opening is not fully closed due to the low swelling rate of the tampon. As a result, the menstrual blood may leak. In the tampon of the related art, on the other hand, the menstrual blood hardly migrates into the central portion of the tampon so that the absorber in the central portion is not effectively exploited. Since the menstrual blood resides on the surface of the tampon, moreover, the tampon, when extracted after use, may present such a poor appearance as to make the user feel uncomfortable.

SUMMARY OF THE INVENTION

An object of the invention is to provide a tampon which has a high absorption rate and a high swelling rate.

According to a first aspect of the invention, there is provided a sanitary tampon comprising an absorber including an absorbent layer made of an absorbent fibrous material and a hydrophobic liquid-permeable layer covering the absorbent layer, the absorber being formed firstly into a flat shape and then into a column shape, wherein the absorbent layer forming the flat absorber is formed with a plurality of small recesses which open in the surface of the absorbent layer and extend into the absorbent layer.

The flat absorber of the sanitary tampon of the invention is constructed to include the absorbent layer and the hydrophobic liquid-permeable layer on the surface of the former. When the flat absorber is formed into the column shape, however, not only the liquid-permeable layer appears in the column surface but also the surface of the absorbent layer and the liquid-permeable layer enter the inside of the column. According to the first aspect of the invention, moreover, the plurality of small recesses are formed in the surface of the absorbent layer so that they are dispersed and arranged not only in the column surface but also in the inside of the column. As a result, the menstrual blood is not only quickly absorbed from the small recesses opening in the column surface into the inside of the absorbent layer but also introduced into the column through the liquid-permeable layer so that the menstrual blood having penetrated into the column is also quickly absorbed from the small recesses arranged inside of the column into the absorbent layer. On the other hand, even the highly viscous menstrual blood is easily absorbed by catching it in the small recesses. As a result, the absorption rate of the menstrual blood can be raised as the entire tampon so that the tampon can quickly swell to close the vaginal opening.

Preferably, the fiber density of the absorbent layer is higher in peripheral portions of the small recesses than in other portions of the absorbent layer.

Also preferably, the surface of the absorbent layer forming the flat absorber includes upper and lower surfaces, and the small recesses are formed in plurality individually in the upper and lower surfaces. In this case, it is preferable that the small recesses are formed substantially perpendicularly toward the inside of the absorbent layer, and that the fiber density between the small recesses formed from the upper surface and the small recesses formed from the lower surface is higher than the fiber density of other portions of the absorbent layer.

According to a second aspect of the invention, there is provided a sanitary tampon comprising an absorber including an absorbent layer made of an absorbent fibrous material and a hydrophobic liquid-permeable layer covering the absorbent layer, the absorber being formed firstly into a flat shape and then into a column shape, wherein the absorbent layer forming the flat absorber includes upper and lower surface portions and a central portion sandwiched between the surface portions, and the fiber density of the central portion is higher than the fiber density of the surface portions.

According to a third aspect of the invention, there is provided a sanitary tampon comprising an absorber including an absorbent layer made of an absorbent fibrous material and a hydrophobic liquid-permeable layer covering the absorbent layer, the absorber being formed firstly into a flat shape and then into a column shape, wherein the absorbent layer forming the flat absorber includes upper and lower surface portions and a central portion sandwiched between the surface portions, and fibers of the central portion are thinner than fibers of the surface portions.

In the absorbent layer according to the second or third aspect of the invention, the surface portions of a low density or thick fibers has a high permeability for the menstrual blood so that the menstrual blood is easily introduced into the central portion of a high density or thin fibers. This central portion spreads all over the column-shaped tampon, and the central portion is located just inside of the surface of the column-shaped tampon. As a result, the tampon can allow quick penetration of the menstrual blood and can quickly swell to close the vaginal opening.

In the tampon according to the second or third aspect of the invention, it is preferable that in the flat absorber, a region of the higher fiber density or a region of the thinner fibers extends planarly or linearly in a flat direction at the central portion of the absorbent layer. In this construction, in the foregoing region of the higher fiber density or the thinner fibers, the menstrual blood is easily introduced to spread planarly or linearly all over the tampon so that the menstrual blood absorption capacity of the entire tampon can be increased.

In the tampon according to the third aspect of the invention, it is preferable that the fibers of the central portion of the absorbent layer have an average thickness of 0.5 to 3 deniers whereas the fibers of the surface portions have an average thickness of 2 to 6 deniers.

In the tampon according to the second or third aspect of the invention, moreover, it is preferable that the absorbent layer forming the flat absorber is formed with a plurality of small recesses which open in the surface of the absorbent layer and extend so far as the region of the higher fiber density or the thinner fibers in the absorbent layer.

DESCRIPTION OF THE PREFERRED EMBODIMENTS

Figure 1:
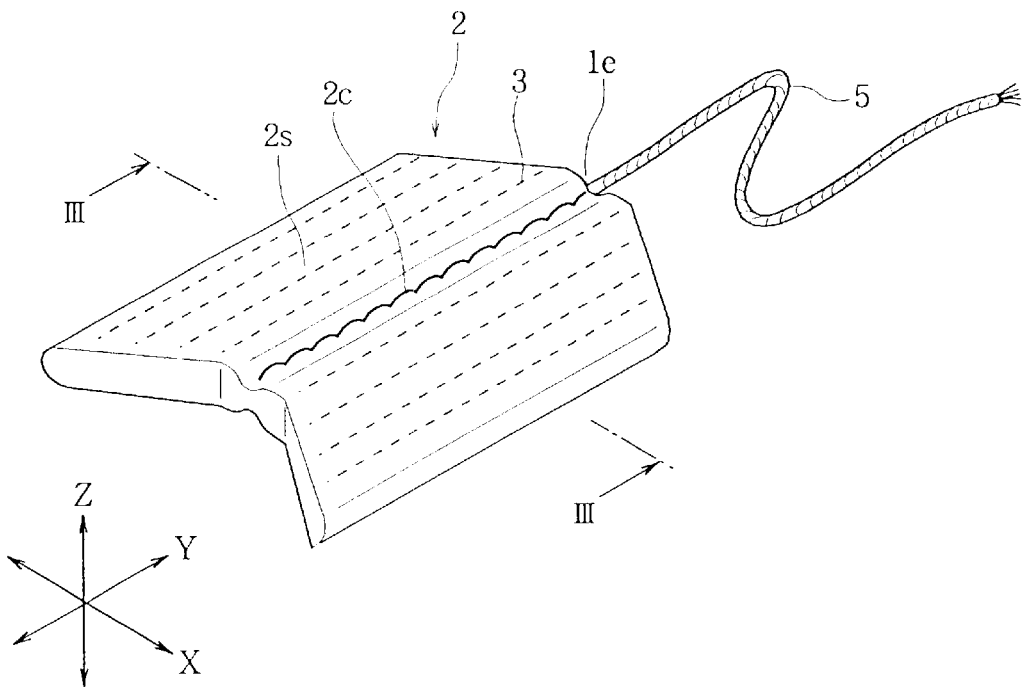
FIG. 1 is a perspective view showing an absorber in a flat state before it is formed into a column shape to produce a tampon according to a first embodiment of the invention.
Figure 2:
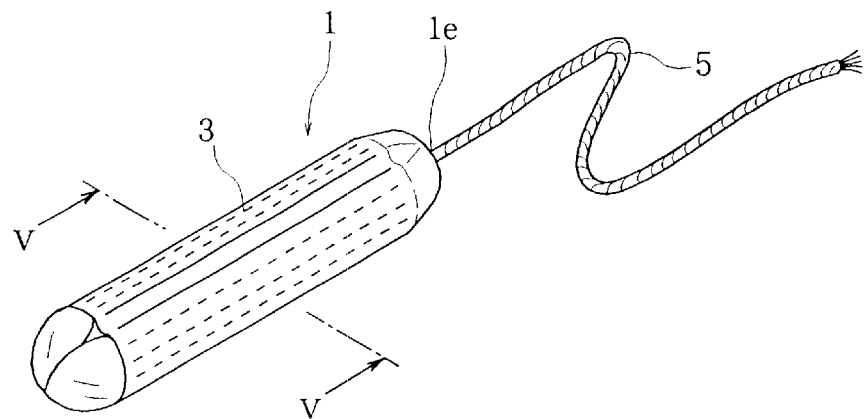
FIG. 2 is a perspective view showing a tampon according to a first embodiment of the invention.
Figure 3:
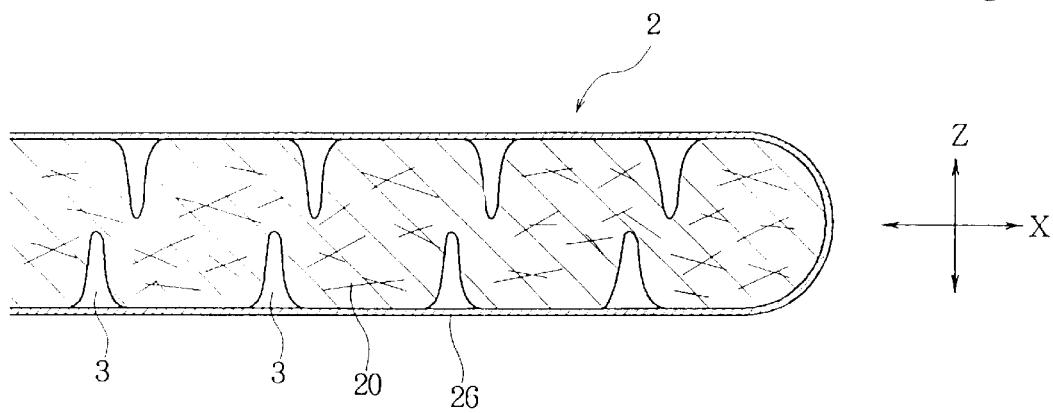
FIG. 3 is a partially enlarged sectional view along line III—III of FIG. 1.
Figure 4:
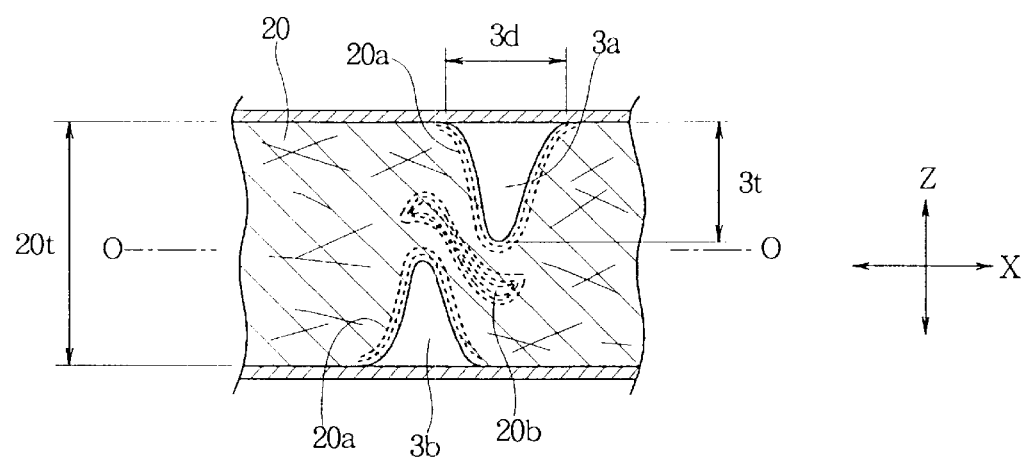
FIG. 4 is an enlarged sectional view of a portion of FIG. 3.

FIG. 1 is a perspective view showing an absorber in a flat state before it is formed into a column shape to produce a tampon according to a first embodiment of the invention; FIG. 2 is a perspective view showing a tampon according to a first embodiment of the invention which has been formed into a column shape from the absorber shown in FIG. 1; FIG. 3 is a partially enlarged sectional view along line III—III of FIG. 1; FIG. 4 is an enlarged sectional view of a portion of FIG. 3; and FIG. 5 is a sectional view along line V—V of FIG. 2.

Figure 5:
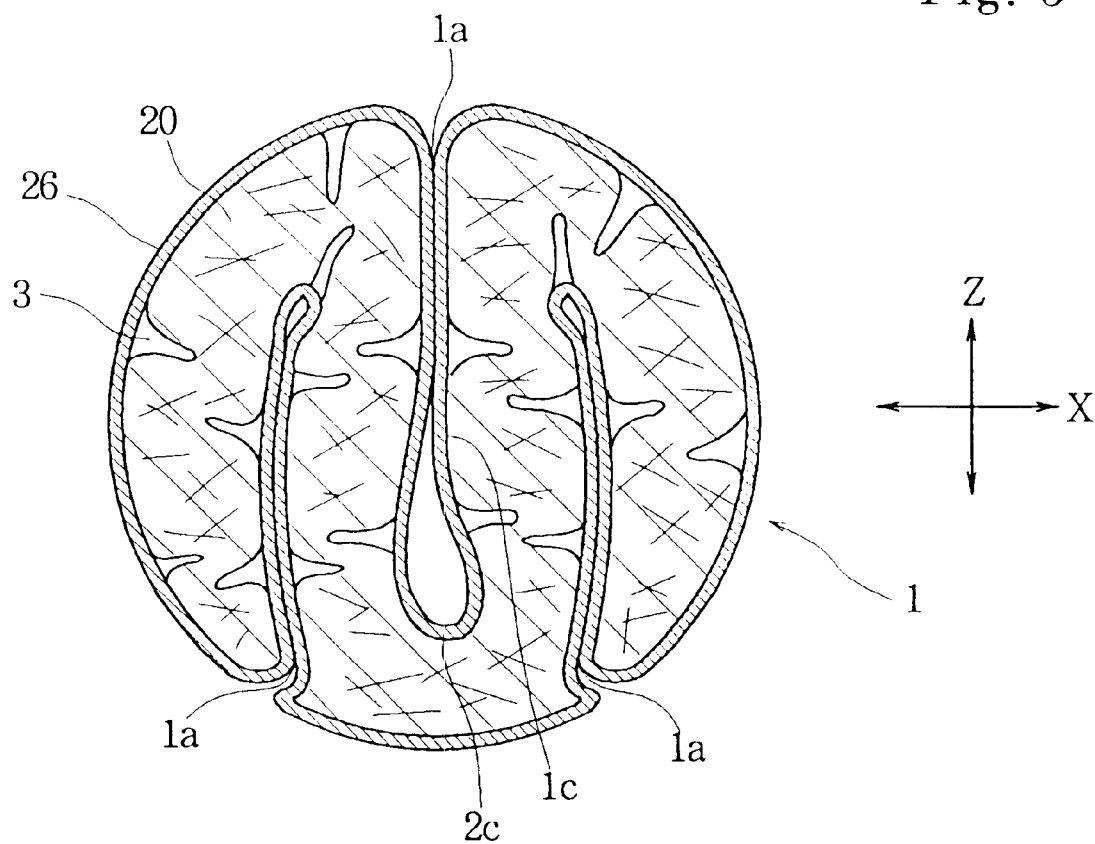
FIG. 5 is a sectional view along line V—V of FIG. 2.

A tampon 1, as shown in FIG. 2, according to a first embodiment of the invention, is so shaped that a flat absorber 2 shown in FIG. 1 is bent generally into a M-shape, as shown in the sectional view of FIG. 5, and then compressed into a column shape. This absorber 2 is formed, as shown in the sectional view of FIG. 3, of an absorbent layer 20 made mainly of a hydrophilic fibrous material, and a hydrophobic liquid-permeable layer covering the absorbent layer 26.

The absorbent layer 20 comprises a fibrous web made of an absorbent fibrous materials such as hydrophilic fibers such as rayon or cotton. In this absorbent layer 20, however, either hydrophobic fibers or hydrophilized hydrophobic fibers may be mixed with the hydrophilic fibers. The term "hydrophilized hydrophobic fiber" as used herein means a hydrophobic fiber subjected to a hydrophilic treatment. In this hydrophilic treatment, a hydrophobic fiber is made hydrophilic, for example, by treating it with a surfactant; by chemically binding a chemical substance such as a monomer or a polymer having a hydrophilic group thereto; by subjecting it to plasma processing; by kneading it with a chemical substance having a hydrophilic group; or by treating its surface to have a profiled section. In the absorbent layer 20, on the other hand, there may be mixed chemicals having a water absorbing function, such as highly water-absorbing polymers.

The absorbent layer 20 is formed by piling a plurality of, e.g., about five to nine fibrous webs preferably having a "basis weight" of 700 to 1,000 g/m$^2$ and a thickness of about 0.07 to 0.09 cm to have a thickness 20t preferably of about 0.4 to 0.7 cm. However, the absorbent layer 20 may be formed of a single fibrous web.

In the upper and lower surfaces of the absorbent layer 20 of the absorber 2, as shown in FIG. 3 and FIG. 4, there are formed a plurality of small recesses 3 which open in the flat surfaces and extend into the absorbent layer 20. These small recesses are formed in plurality all over the surface of the absorbent layer 20, as seen through the liquid-permeable layer 26 in FIG. 1.

The small recesses 3 can be formed by embossing the absorbent layer 20. For example, the absorbent layer 20 is pressed through rolls or pressure plates having a number of bosses on their surfaces. Alternatively, the absorbent layer 20 is pressed by using needles. This embossing treatment is carried out by not or slightly heating the rolls, the pressure plates or the needles. When the small recesses 3 are thus formed by pressing the absorbent layer 20, the fiber density becomes high at the peripheral portions 20a of the small recesses 3, as shown in the enlarged view of FIG. 4.

The small recesses 3 preferably have a depth 3t of 1 to 5 mm and more preferably have a depth 3t of 2 to 3 mm. On the other hand, the small recesses 3 in the surface of the absorbent layer 20 preferably have an opening diameter 3d of 0.5 to 1.0 mm. Moreover, the small recesses 3 preferably have a density of 1 to 10 recesses/cm$^2$, more preferably have a density of 2 to 3 recesses/cm$^2$.

When the small recesses 3 are formed in the upper and lower surfaces of the absorbent layer 20, it is preferable that small recesses 3a in one surface and small recesses 3b in the other surface are opposed to each other. Here in FIG. 4, these small recesses 3a and 3b are opposed with a small offset in an X direction, and they may be arranged incompletely in a face-to-face relation. If the small recesses 3a in one face and the small recesses 3b in the other face are thus formed substantially in the face-to-face relation, as shown in FIG. 4, the fiber density is higher in portions 20b between the small recesses 3a and 3b opposed from the two surfaces to each other. Since the small recesses 3 are formed all over the upper and lower surfaces of the absorbent layer 20, moreover, the density is liable to become relatively high at the portion including the center O—O (as will be called the central portion) in the thickness direction (or a Z direction) of the absorbent layer 20 but relatively low in the surface portions.

For example, the absorbent layer, which has been prepared by piling fibrous webs having the aforementioned preferable basis weight, density and thickness to have the aforementioned preferable thickness (0.4 to 0.7 mm), is preferably pressed with needles to give a density of 0.40 to 0.60 g/cm$^3$ and a basis weight of 500 to 700 g/m$^2$ in the vicinity of the center (over a thickness of 0.5 to 1.5 mm across the center O—O in the thickness direction) in the thickness direction of the absorbent layer 20, and a density of 0.05 to 0.20 g/cm$^3$ and a basis weight of 100 to 200 g/m$^2$ in the vicinity of the surface (over a thickness of 1.5 to 2.5 mm from the individual surfaces of the absorbent layer 20) of the absorbent layer 20. Here, the entire thickness 20$t$ of the absorbent layer 20 is hardly changed immediately after the embossing or needle pressing treatment.

The absorbent layer 20 having the small recesses 3 thus formed is covered on its surface with the liquid-permeable layer 26 to provide the absorber 2. The liquid-permeable layer 26 is formed of: a spun lace, air-through, point bond, spun bond or thermal bond nonwoven fabric made of hydrophobic fibers such as polyester, polypropylene and polyethylene terephthalate; a nonwoven fabric made of such material and having a number of pores; or a porous plastic sheet. Here in this embodiment, the small recesses 3 are formed exclusively in the absorbent layer 20 but may be formed by embossing the surface of the absorber 2 after the absorbent layer 20 was covered with the liquid-permeable layer 26.

The absorber 2 thus obtained is cut into an arrow feather shape, as shown in FIG. 1. After this, the tampon 1 shown in FIG. 2 is manufactured by folding the absorber 2 along three lines extending in a Y direction so as to have M-shaped sectional view of FIG. 5, and by compressing the absorber 2 thus folded to about one third volume (for example, the volume of about 12 cm$^3$ before compression is compressed to about 4 cm$^3$) into a column shape. Here, if the absorber 2 is compressed while being fed with moisture, the fibers are hydrogen-bonded to each other so that the tampon 1 compressed hardly restores its bulk. As the absorbent layer 20 absorbs the menstrual blood, moreover, the hydrogen bonds of the fibers are broken so that it swells to restore the original bulk thereby to close the vaginal opening.

The tampon 1 thus obtained has a diameter of about 11 to 13 mm and an entire Y-direction length (excepting a string 5) of about 5 cm. On the other hand, the tampon 1 preferably has an overall density of 0.30 to 0.50 g/cm$^3$. Here in the compression shaping, it is preferable that the aforementioned density gradient relation (that is, the density of the absorbent layer 20 is higher in the vicinity of the center O—O but lower in the vicinity of the surface) of the absorbent layer 20 is not broken. For example, the aforementioned preferred densities, immediately after forming the small recesses 3, in the vicinity of the center O—O and in the vicinity of the surface are preferably changed to be about 0.50 to 0.75 g/cm$^3$ and about 0.15 to 0.60 g/cm$^3$, respectively.

As in the ordinary tampon, moreover, in the tampon of the invention, the string 5 to be used to pull out the used tampon from the vaginal opening is stitched along a center line 2$c$ of the absorber 2, as shown in FIG. 1. This string 5 is extended, after the column shape was formed by compression, from a rear end portion 1$e$ of the tampon 1, as shown in FIG. 2.

In the tampon 1 thus obtained, the menstrual blood passes through the liquid-permeable layer 26 on the surface of the tampon 1 and is introduced into the small recesses 3 which are numerously formed in the absorbent layer 20, so that it is absorbed in the surface and the small recesses 3 of the absorbent layer 20. Since the portions 20$a$ in the vicinity of the small recesses 3 of the absorbent layer 20 are highly dense, as has been described hereinbefore, the menstrual blood is more introduced into the small recesses 3 so that it is liable to migrate into the central portion of the absorbent layer. Here, the menstrual blood can be caught, even if highly viscous, by the small recesses 3. Since the flat absorber 2 is folded to have a M-shaped sectional view and then compressed into a column shape, moreover, the surface of the absorbent layer 20 enters the inside of the column-shaped tampon 1 and therefore, the small recesses 3 are dispersed widely and homogeneously not only in the column surface of the column-shaped tampon 1 but also in the inside portion (including the center 1$c$) of the column. Since the menstrual blood penetrates from the portions, as indicated by numeral 1$a$, of the tampon 1 into the inside of the column along the liquid-permeable layer 26, it is quickly absorbed from the small recesses 3 located inside of the column into the absorbent layer 20.

Moreover, the absorbent layer 20 of the tampon 1 is denser, even after compressed into the column shape, in the vicinity of the center O—O than in the vicinity of the surface, and the central portion is widely present in the column-shaped tampon. Even in any portion of the tampon 1, therefore, the menstrual blood is liable to flow to the denser central portion of the absorbent layer 20.

As a result, in the tampon 1 according to a first embodiment of the invention, the menstrual blood is absorbed not only by the surface of the absorbent layer 20 but also by the central portion thereof and further by the inside portion (including the center 1$c$) of the tampon 1 so that the absorbent layer 20 can be effectively exploited to raise the absorbing rate of the menstrual blood. Therefore, the swelling rate of the tampon 1 can be raised to close the vaginal opening within a short time. On the other hand, the menstrual blood is introduced into the central portion of the absorbent layer so that it can hardly reside in the surface of the tampon 1 (i.e., in the surface of the absorbent layer 20) thereby to lessen an uncomfortableness which might otherwise be given to the user after use.

Here in the embodiment, the small recesses 3 are formed in the surface of the absorbent layer 20 by pressing the absorbent layer 20. However, the absorbent layer 20 may be exemplified by a fibrous web formed on the face having numerous bosses formed thereon, that is, a fibrous web having the small recesses 3 formed in advance.

Figure 6:
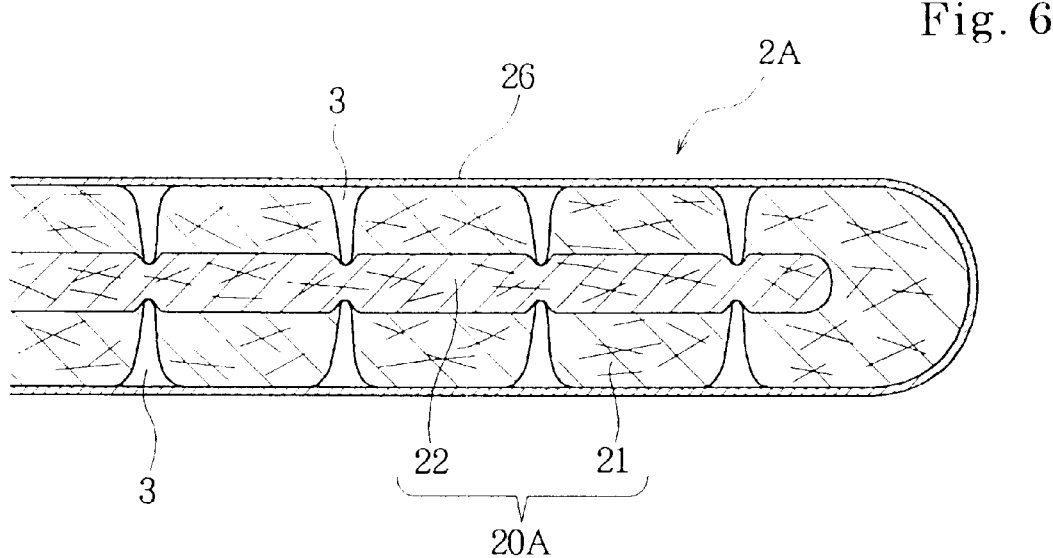
FIG. 6 is a partially enlarged sectional view of an absorber in a flat state before it is formed into a column shape to produce a tampon according to a second embodiment of the invention.
Figure 7:
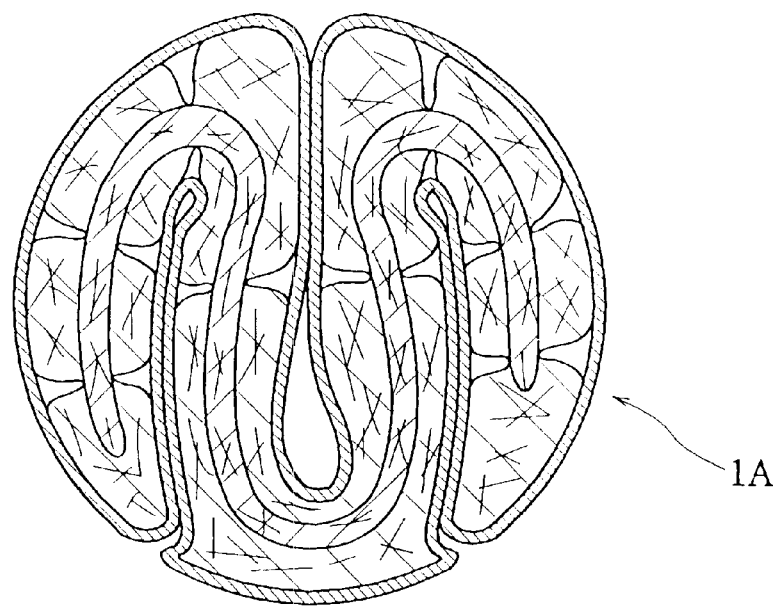
FIG. 7 is a sectional view showing a tampon according to a second embodiment of the invention.

FIG. 6 is a partially enlarged sectional view showing an absorber 2A in a flat state before it is formed into a column shape to produce a tampon according to a second embodiment of the invention, and FIG. 7 is a sectional view showing a tampon 1A according to a second embodiment of the invention, which is formed by compressing the absorber 2A of FIG. 6 into a column shape. An absorbent layer 20A of the absorber 2A shown in FIG. 6 is constructed to include a surface layer 21 and a center layer 22 having a higher fibrous density than that of the surface layer. These individual layers are made of an absorbent fiber material as in the aforementioned absorbent layer 20.

The difference in the density between the center layer 22 and the surface layer 21 can be obtained by piling fibrous webs of different densities. Preferably, for example: the center layer 22 is made of a fibrous web having a density of 0.40 to 0.60 g/cm$^3$, a basis weight of 500 to 700 g/m$^2$ and a thickness of 0.5 to 1.5 mm; the surface layer 21 is made of a fibrous web of a density of 0.05 to 0.20 g/cm$^3$, a basis weight of 100 to 200 g/m$^2$ and a thickness of about 1.5 to 2.5 mm; and the center layer 22 is sandwiched between the two surface layers 21. The resultant absorbent layer 20A obtained has a thickness of about 0.4 to 0.7 mm. By making this density gradient, the menstrual blood is liable to migrate from the surface layers 21 of the lower density to the center layer 22.

Here, it is preferable that the small recesses 3 are also formed in the absorbent layer 20A as in the first embodiment. The small recesses 3 are formed substantially perpendicularly in the thickness direction (or the Z-direction) from the surface of the absorbent layer 20A so that their leading ends extend so far as the center layer 22. As a result, the menstrual blood having been introduced into the small recesses 3 more easily migrates to the center layer 22 of the absorbent layer 20A. In this second embodiment, however, the absorbing rate of the menstrual blood is sufficiently high even without the small recesses 3, because of the density gradient between the center layer 22 and the surface layers 21.

As in the first embodiment, then, the tampon 1A can be manufactured by covering the surface of the absorbent layer 20A with the liquid-permeable layer 26 to form the absorber 2A and by shaping the absorber 2A, as shown in FIGS. 1 and 5. In the tampon 1A thus obtained, the center layer for attracting the menstrual blood extends all over so that the tampon 1A has a high menstrual blood absorbing rate and a high swelling rate in its entirety. On the other hand, the menstrual blood is liable to migrate into the center layer 22 so that little color is left in the tampon surface while making the user feel little uncomfortable after use.

Unlike the second embodiment in which the densities of the center layer 22 and the surface layers 21 are made different as shown in FIG. 6, according to a third embodiment of the invention, the thickness of the fibers composing the center layer 22 can be made smaller than that of the fibers composing the surface layers 21. The thinner fibers will easily attract and hold the menstrual blood by the capillary phenomenon. Even if the fibrous webs composing the center layer 22 and the surface layers 21 have an equal fibrous density, therefore, the menstrual blood is lead from the surface layers 21 into the center layer 22 when the fibers composing the center layer 22 are thinner than those composing the surface layers 21.

It is preferable that the fibers of the center layer 22 have an average thickness of 0.5 to 3 deniers whereas the fibers of the surface layers 21 have an average thickness of 2 to 6 deniers, for example. When the small recesses 3 are formed, moreover, it is preferable that the leading ends of the small recesses extend so far as the center layer 22 as in the second embodiment.

In the third embodiment, too, the densities of the fibrous webs of the center layer 22 and the surface layers 21 may be different as in the second embodiment. In this case, the functional difference between the center layer 22 and the surface layers 21 can be exhibited even if the density difference between the center layer 22 and the surface layers 21 is not so large as that of the second embodiment.

Figure 8:
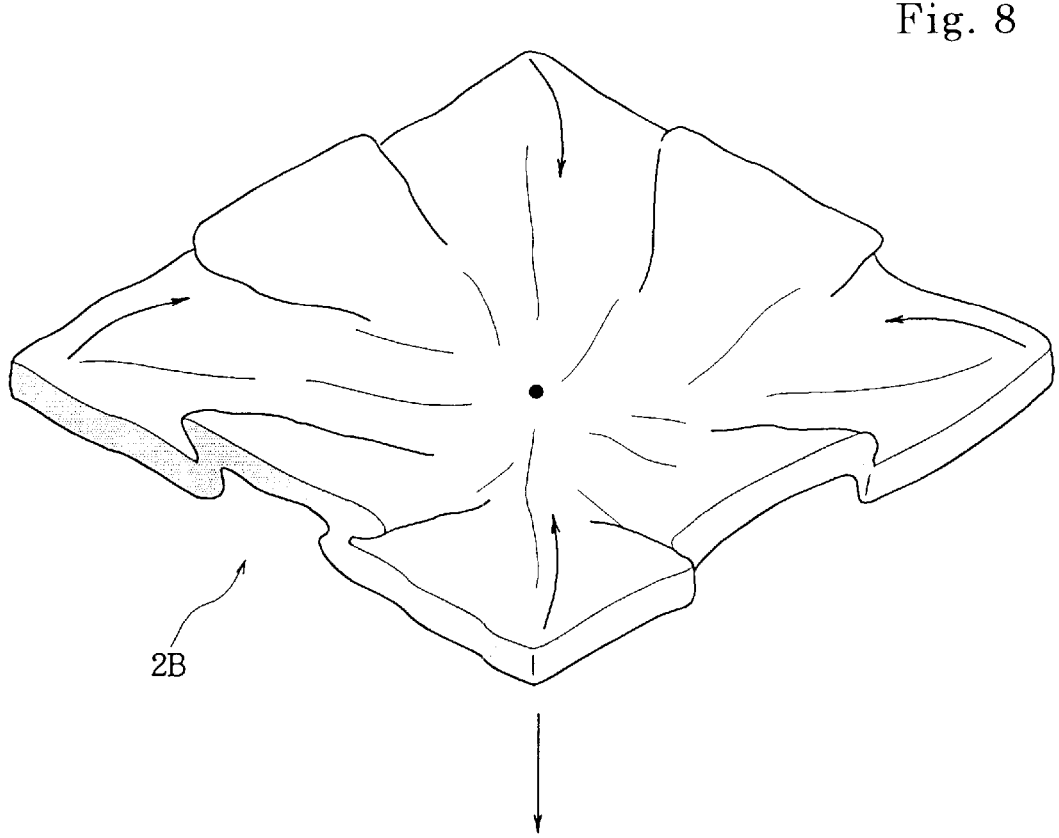
FIG. 8 is a perspective view for explaining a method for manufacturing a tampon according to another embodiment of the invention.
Figure 9A:
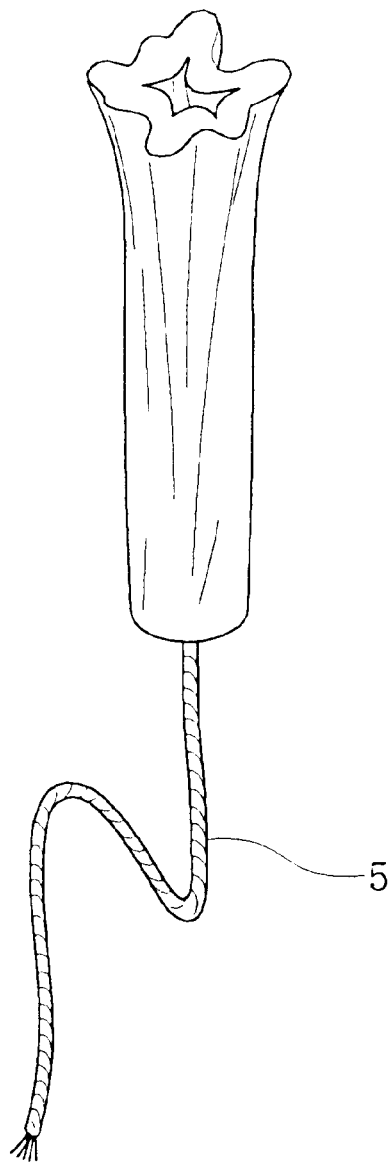
FIG. 9A is a perspective view for explaining a method for manufacturing a tampon according to another embodiment of the invention.
Figure 9B:
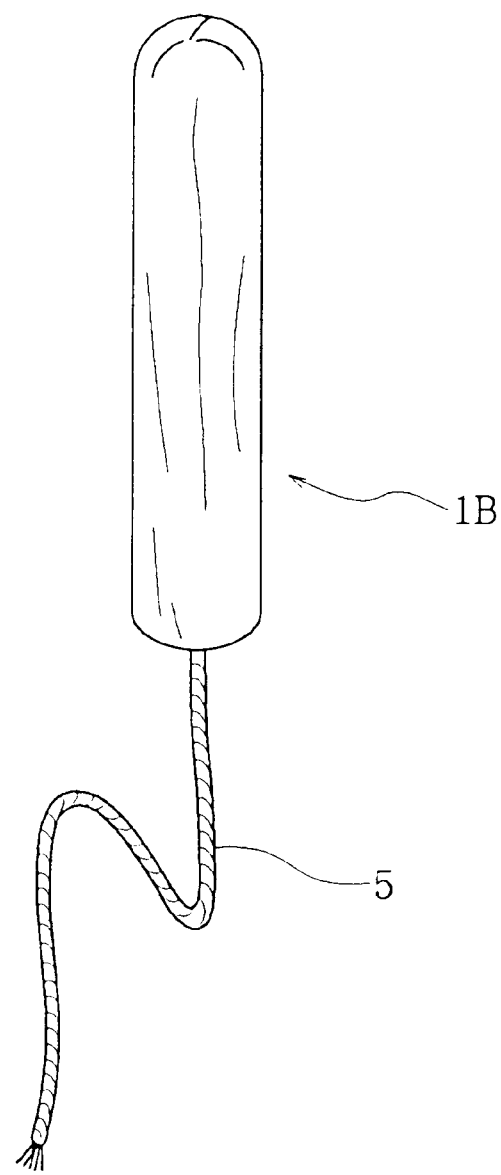
FIG. 9B is a perspective view showing a completed tampon according to another embodiment of the invention.

In order to manufacture the tampon of the invention, in addition, various methods can be employed to form the flat absorbers which have been described in connection with the foregoing first to third embodiments into a column shape. As shown in FIG. 8, for example, a flat absorber 2B cut into a square shape is attached with the string 5 at the central portion thereof and is then drawn as indicated by the arrows to form the string-attached portion into the rear end portion of the column shape, as shown in FIG. 9A. After this, the peripheral end of the leading portion of the absorber 2B can be compressed to be round, thereby to manufacture the tampon 1B shown in FIG. 9B.

Figure 10:
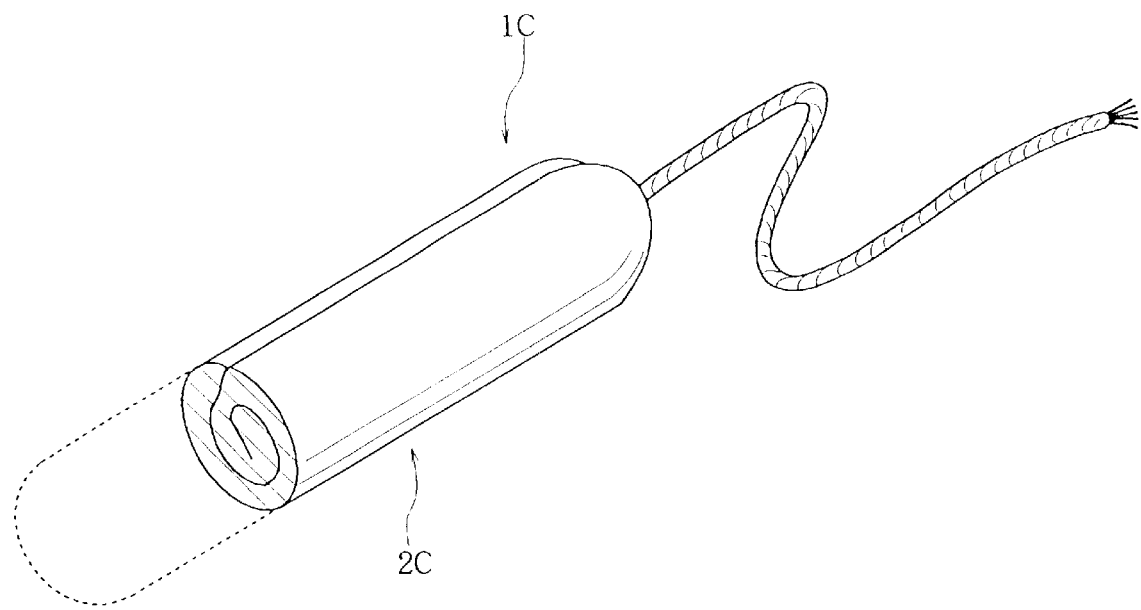
FIG. 10 is a perspective view for explaining a method for manufacturing a tampon according to still another embodiment of the invention.

As shown in FIG. 10, moreover, a flat absorber 2C, as shown in FIG. 1, may be helically rounded to form a tampon 1C.

EXAMPLE

A tampon according the first embodiment of the invention was manufactured in the following manner. There was prepared a fibrous web made of rayon and having a basis weight of 950 g/m$^2$ and a thickness of 5 mm. An absorber was obtained by covering the fibrous web all over its surface with a spun bond nonwoven fabric made of polyethylene terephthalate and having a basis weight of 12 g/m$^2$. Small recesses were formed in the surface of the absorber by clamping and compressing the absorber from the upper and lower surfaces thereof with needles formed in a density of 4 needles/cm$^2$. At this time, the thickness was unvaried at 5 mm, and the density was 0.125 g/cm$^3$ in the vicinity of the center (over a thickness of about 1 mm) and 0.45 g/cm$^3$ in the vicinities of the upper and lower surfaces (individually over a thickness of about 2 mm). After this, the absorber was compressed and formed generally into a M shape, as shown in FIG. 5, to manufacture the tampon as shown in FIG. 2. This tampon had a longitudinal size of 5 cm, a diameter of 12 mm and an overall density of 0.40 g/cm$^3$. The following tests were made to examine the absorbing performance of the tampon.

(Quantity of Absorption)

The quantity of artificial menstrual blood to be absorbed by the tampon was metered.

(Factor of Absorption)

The quantity of artificial menstrual blood to be absorbed with respect to the weight of the tampon itself was calculated and indicated in terms of the factor.

(Absorptivity Test)

The tampon was inserted and fitted in a rubber tube, and a uniform pressure (200 m/q) was applied to the tampon from the outside of the rubber tube. 2 cc, 6 cc or 10 cc of artificial menstrual blood was injected all at once from the upper portion of the rubber tube by using an injector. The time period from the start of the injection to the end of the absorption was measured.

Here, a tampon having no small recess was subjected to the same tests for comparison. This tampon for comparison was prepared by covering a flat absorbent layer having a basis weight of 950 g/m$^2$, a thickness of 5 mm and a density of 0.19 g/cm$^3$ with the liquid-permeable layer as in Example, and by compressing and forming it into a column shape.

TABLE 1

| | Weight (g) | Quantity of Absorption (g) | Absorption Factor | Absorption Rate (sec) 2 cc | 6 cc | 10 cc |
| --- | --- | --- | --- | --- | --- | --- |
| Comp. | 3.28 | 18.7 | 4.7 | 18 | 48 | 84 |
| Ex. | 3.22 | 18.4 | 4.71 | 12 | 29 | 75 |

As a result of the various structures described in detail above, advantages of the invention may include one or more the following:

(a) The menstrual blood is liable to be introduced into the central portion of the absorber forming the tampon so that the menstrual blood absorption rate and the swelling rate of the tampon are high;

(b) Not only the surface of the absorber but also the inside of the same can be effectively exploited;

(c) The menstrual blood does not reside on the surface of the tampon so that little color is left in the surface of the used tampon so that the user hardly feel uncomfortable; and (d) When the small recesses are formed, they can confine highly viscous menstrual blood.

Here, comprises/comprising when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. A sanitary tampon comprising:

a single layer absorber folded into a plurality of layers and compressed into a column shape over its entirety while maintaining a layered structure, said single layer absorber including an absorbent layer made of an absorbent fibrous material and a hydrophobic liquid-permeable layer covering both surfaces of the absorbent layer, the absorbent layer having a plurality of small open recesses in both surfaces of the absorbent layer and extending toward an inner area of the absorbent layer, wherein prior to compression, the small open recesses have an opening diameter of 0.5 to 1.0 mm and a depth 1 to 5 mm, and are distributed in a density of 1 to 10 recesses/cm$^2$.

2. A sanitary tampon as set forth in claim 1, wherein the absorbent layer is formed of a fibrous web comprising rayon, and the hydrophobic liquid-permeable layer is formed of a spunbonded nonwoven fabric comprising polyethylene terephthalate.

3. A sanitary tampon as set forth in claim 1, wherein the absorber is folded into a general M shape so as to have four layers stacked one on another.

4. A sanitary tampon comprising:

a single layer absorber folded into a plurality of layers and compressed into a column shape over its entirety while maintaining a layered structure, said single layer absorber including an absorbent layer made of an absorbent fibrous material and a hydrophobic liquid-permeable layer covering both surfaces of the absorbent layer, the absorbent layer having a plurality of small open recesses in both surfaces of the absorbent layer and extending toward an inner area of the absorbent layer, wherein the small open recesses are formed by embossing the absorbent layer prior to compression so that a fiber density of the absorbent layer is increased in a vicinity of the small open recesses.

5. A sanitary tampon as set forth in claim 4, wherein the fiber density of the absorbent layer is also increased at positions between small open recesses formed in one face of the absorbent layer and respective corresponding small recesses formed in another face of the absorbent layer.

6. A sanitary tampon as set forth in claim 4, wherein the absorbent layer is formed of a fibrous web comprising rayon, and the hydrophobic liquid-permeable layer is formed of a spunbonded nonwoven fabric comprising polyethylene terephthalate.

7. A sanitary tampon as set forth in claim 4, wherein the absorber is folded into a general M shape so as to have four layers stacked one on another.

* * * * *